(12) United States Patent
Chiou

(10) Patent No.: US 12,029,807 B2
(45) Date of Patent: Jul. 9, 2024

(54) NO-RINSE MAKEUP REMOVAL COMPOSITION

(71) Applicant: L'OREAL, Paris (FR)

(72) Inventor: Catherine Chiou, Saddle Brook, NJ (US)

(73) Assignee: L'OREAL, Paris (FR)

( * ) Notice: Subject to any disclaimer, the term of this patent is extended or adjusted under 35 U.S.C. 154(b) by 141 days.

(21) Appl. No.: 17/553,425

(22) Filed: Dec. 16, 2021

(65) Prior Publication Data

US 2023/0190627 A1    Jun. 22, 2023

(51) Int. Cl.
| | |
|---|---|
| *A61K 8/891* | (2006.01) |
| *A61K 8/06* | (2006.01) |
| *A61K 8/31* | (2006.01) |
| *A61K 8/37* | (2006.01) |
| *A61K 8/86* | (2006.01) |
| *A61K 8/894* | (2006.01) |
| *A61Q 1/14* | (2006.01) |

(52) U.S. Cl.
CPC .............. *A61K 8/891* (2013.01); *A61K 8/064* (2013.01); *A61K 8/31* (2013.01); *A61K 8/37* (2013.01); *A61K 8/375* (2013.01); *A61K 8/86* (2013.01); *A61K 8/894* (2013.01); *A61Q 1/14* (2013.01)

(58) Field of Classification Search
None
See application file for complete search history.

(56) References Cited

U.S. PATENT DOCUMENTS

| | | | | |
|---|---|---|---|---|
| 2011/0150800 A1* | 6/2011 | Dumousseaux | ....... | A61K 8/894 424/78.03 |
| 2013/0164233 A1* | 6/2013 | Lee | ........................ | A61Q 19/02 424/62 |
| 2017/0189295 A1 | 7/2017 | Bernard et al. | | |
| 2019/0201304 A1* | 7/2019 | Sverdlove | .............. | A61K 8/365 |
| 2022/0096357 A1 | 3/2022 | Chiou | | |

FOREIGN PATENT DOCUMENTS

| | | | |
|---|---|---|---|
| CN | 112294732 A | * | 2/2021 |
| DE | 102015222073 A1 | | 5/2017 |
| EP | 1034774 B1 | | 5/2002 |

OTHER PUBLICATIONS

An internet product sheet, "ABIL® WE 09 MB", obtained from the website: https://glenncorp.com/shop/abil-we-09-mb/ (date unknown).*
English translation for CN-112294732 A (2021).*
Tandy et al ("Extraction of Heavy Metals from Soils Using Biodegradable Chelating Agents", Environ. Sci. Technol. vol. 38 (2004), p. 937-944). (Year: 2004).*
Search Report issued to French counterpart Application No. FR 2205080 dated Jan. 20, 2023.
PCT Notification of Transmittal of the International Search Report and the Written Opinion of the International Searching Authority, or the Declaration issued to counterpart Application No. PCT/IB2022/062326 dated Jan. 31, 2023.

* cited by examiner

*Primary Examiner* — Sin J Lee

(74) *Attorney, Agent, or Firm* — McNees Wallace & Nurick LLC

(57) ABSTRACT

A makeup removal composition includes at least one silicone crosspolymer-based emulsifier, at least one polyglyceryl ester with HLB less than 10, at least one branched or linear liquid alkane with carbon chain length of C11 to C20, at least one polar emollient ester with carbon chain length of C12 to C24, water, or water and a water-based hydrating agent or solvent or combination thereof, and, optionally one or more additives.

19 Claims, No Drawings

NO-RINSE MAKEUP REMOVAL COMPOSITION

FIELD

This invention relates to a hydrating no-rinse makeup removal composition.

BACKGROUND

Removal of stubborn makeup has always been a challenge and a consumer pain point, particularly for mascara and waterproof mascara, long-wear foundation and longer-lasting lip products. Typical makeup removal products are ineffective in removing stubborn makeup, thus requiring repeated tugging and rubbing on the skin and/or the delicate eye areas, causing irritation. Some oil-based makeup removing products may provide ease of makeup removal but leave behind an unpleasant and greasy skin feel. Less greasy alternatives smudge and leave makeup residue. Many of the existing and compositions also require rinsing after use. Accordingly, there is a need for compositions that will provide easy and efficacious makeup removal in addition to a soft and smooth skin feel after the use after the use and do not require subsequent washing or rinsing.

SUMMARY

To address the deficiencies in the art with makeup removal products, the inventors provide a hydrating no-rinse (leave on) makeup removal composition that provides easy and efficacious makeup removal and a soft and smooth skin feel after the use. Use of the composition does not require use of water for rinsing after cleansing, therefore saving water usage and making cleansing possible under conditions where water is scarce or may not be available.

In various embodiments according to the invention, the disclosure provides a no-rinse makeup removal composition that includes at least one silicone crosspolymer-based emulsifier, at least one polyglyceryl ester with HLB less than 10, at least one branched or linear liquid alkane with carbon chain length of C11 to C20, at least one polar emollient ester with carbon chain length of C12 to C24, water, or water and a water-based hydrating agent or solvent or combination thereof, and, optionally one or more additives.

In some embodiments, the at least one silicone crosspolymer-based emulsifier is selected from the group consisting of dimethicone/PEG-10/15 crosspolymer, dimethicone/polyglycerin-3 crosspolymer, and combinations thereof, and wherein the at least one polyglyceryl ester with HLB less than 10 is selected from the group consisting of polyglyceryl-6 polyricinoleate, polyglyceryl-3 diisostearate, polyglyceryl-2 oleate, polyglyceryl-2 stearate and combinations thereof.

In some embodiments, the at least one branched or linear liquid alkane with carbon chain length of C11 to C20 is selected from the group consisting of isohexadecane, isododecane, undecane, tridecane, C15-19 alkane, and combinations thereof, and wherein the at least one polar emollient ester with carbon chain length of C12 to C24 is selected from the group consisting of isopropyl myristate, ethylhexyl palmitate, isopropyl palmitate, hexyl laurate, triethyl citrate, diisopropyl adipate, diisopropyl sebacate, dicaprylyl carbonate, isopropyl isostearate, isononyl isononanoate, neopentyl glycol diheptanoate and combinations thereof.

In some embodiments, the at least one silicone crosspolymer-based emulsifier comprises dimethicone/PEG-10/15 crosspolymer, and the at least one polyglyceryl ester with HLB less than 10 comprises polyglyceryl-6 polyricinoleate, and the at least one branched or linear liquid alkane with carbon chain length of C11 to C20 comprises isohexadecane, and the at least one polar emollient ester with carbon chain length of C12 to C24 comprises ethylhexyl palmitate.

In some embodiments, the at least one silicone crosspolymer-based emulsifier is present from about 0.1% to about 10%, by weight of the composition.

In some embodiments, the at least one polyglyceryl ester with HLB less than 10 is present from about 0.1% to about 5%, by weight of the composition.

In some embodiments, the at least one branched or linear liquid alkane with carbon chain length of C11 to C20 is present from about 5% to about 15% by weight of the composition.

In some embodiments, the at least one polar emollient ester with carbon chain length of C12 to C24 is present from about 1% to about 10% by weight of the composition.

In some embodiments, the water, or water and a water-based hydrating agent or solvent or combination thereof is present from about 65% to about 85% by weight of the composition.

In some embodiments, the water, or water and a water-based hydrating agent or solvent or combination thereof comprises water, and at least one hydrating agent, the at least one hydrating agent present from about 5% to about 20% by weight of the composition.

In various embodiments according to the invention, the composition is a water-in-oil (silicone) emulsion comprising (a) a water phase that comprises the water, or water and a water-based hydrating agent or solvent or combination thereof, and (b) a silicone oil phase comprising the at least one silicone crosspolymer-based emulsifier, the at least one polyglyceryl ester with HLB less than 10, the at least one branched or linear liquid alkane with carbon chain length of C11 to C20, and the at least one polar emollient ester with carbon chain length of C12 to C24.

In some embodiments, the composition has a phase ratio of the total weight of the water phase to the total weight of the silicone oil phase in a range from about 8.0 to about 1.5.

In some embodiments, the silicone oil phase further comprises one or more oil phase ingredients selected from the group consisting of silicone oils, oil-soluble active ingredients, emollients, and combinations thereof, and one or both the water and silicone oil phases optionally includes one or more of the optional additives, the optional additives selected from the group consisting of pH adjusters, chelating agents, skin care actives, preservatives, fillers, powders, fragrances, dyes, pigments, and combinations thereof.

In some embodiments, the no-rinse makeup removal composition includes at least one silicone crosspolymer-based emulsifier present from about 0.1% to about 10%, by weight of the composition, by weight of the composition, at least one polyglyceryl ester with HLB less than 10 present from about 0.1% to about 5%, by weight of the composition, at least one branched or linear liquid alkane with carbon chain length of C11 to C20 present from about 5% to about 15%, by weight of the composition, at least one polar emollient ester with carbon chain length of C12 to C24 present from about 1% to about 10%, by weight of the composition, water, or water and a water-based hydrating agent or solvent or combination thereof, present from about 65% to about 85% by weight of the composition, and, optionally one or more additives selected from the group consisting of pH adjusters, chelating agents, skin care actives, preservatives, fillers, powders, fragrances, dyes, pigments, and combinations thereof.

In some embodiments, the at least one silicone crosspolymer-based emulsifier is selected from the group consisting of dimethicone/PEG-10/15 crosspolymer, dimethicone/polyglycerin-3 crosspolymer, and combinations thereof.

In some embodiments, the at least one polyglyceryl ester with HLB less than 10 is selected from the group consisting of polyglyceryl-6 polyricinoleate, polyglyceryl-3 diisostearate, polyglyceryl-2 oleate, polyglyceryl-2 stearate, and combinations thereof.

In some embodiments, the at least one branched or linear liquid alkane with carbon chain length of C11 to C20 is selected from the group consisting of isohexadecane, isododecane, undecane, tridecane, C15-19 alkane, and combinations thereof.

In some embodiments, the at least one polar emollient ester with carbon chain length of C12 to C24 is selected from the group consisting of isopropyl myristate, ethylhexyl palmitate, isopropyl palmitate, hexyl laurate, triethyl citrate, diisopropyl adipate, diisopropyl sebacate, dicaprylyl carbonate, isopropyl isostearate, isononyl isononanoate, neopentyl glycol diheptanoate, and combinations thereof.

In some embodiments, the at least one silicone crosspolymer-based emulsifier comprises dimethicone (and) dimethicone/PEG-10/15 crosspolymer present from about 0.5% to about 20%.

In some embodiments, the at least one polyglyceryl ester with HLB less than 10 comprises polyglyceryl-6 polyricinoleate present from about 0.1% to about 20%.

In some embodiments, the at least one branched or linear liquid alkane with carbon chain length of C11 to C20 comprises isohexadecane present from about 5% to about 15%.

In some embodiments, the at least one polar emollient ester with carbon chain length of C12 to C24 comprises isopropyl palmitate present from about 1% to about 10%.

In some embodiments, the water, or water and a water-based hydrating agent or solvent or combination thereof comprises water, and at least one hydrating agent present from about 5% to about 20% by weight of the composition; all amounts by weight, based on the total weight of the composition.

In some embodiments, the at least one silicone crosspolymer-based emulsifier comprises dimethicone (and) dimethicone/PEG-10/15 crosspolymer present at about 3%; the at least one polyglyceryl ester with HLB less than 10 comprises polyglyceryl-6 polyricinoleate present at about 0.2%; the at least one branched or linear liquid alkane with carbon chain length of C11 to C20 comprises isohexadecane present at about 7%; the at least one polar emollient ester with carbon chain length of C12 to C24 comprises isopropyl palmitate present at about 5%; and the water, or water and a water-based hydrating agent or solvent or combination thereof comprises water, and at least one hydrating agent that comprises glycerin present at about 15%. In some embodiments, the composition further comprises one or more additives selected from the group consisting of sodium chloride, sodium citrate, citric acid, tetrasodium glutamate diacetate, piroctone olamine, hydroxyacetophenone, and combinations thereof. In some embodiments, the composition is a water-in oil (silicone) emulsion comprising (a) a water phase that comprises the water, or water and a water-based hydrating agent or solvent or combination thereof, and (b) a silicone oil phase comprising the at least one silicone crosspolymer-based emulsifier, the at least one polyglyceryl ester with HLB less than 10, the at least one branched or linear liquid alkane with carbon chain length of C11 to C20, and the at least one polar emollient ester with carbon chain length of C12 to C24, wherein the composition has a phase ratio of the total weight of the water phase to the total weight of the silicone oil phase in a range from about 8.0 to about 1.5, and wherein the silicone oil phase further comprises one or more oils phase ingredients selected from the group consisting of silicone oils, oil-soluble active ingredients, emollients, and combinations thereof.

In various embodiments according to the invention, the disclosure also provides method for removing makeup, comprising selecting a no-rinse makeup removal composition that includes at least one silicone crosspolymer-based emulsifier, at least one polyglyceryl ester with HLB less than 10, at least one branched or linear liquid alkane with carbon chain length of C11 to C20, at least one polar emollient ester with carbon chain length of C12 to C24, and water, or water and a water-based hydrating agent or solvent or combination thereof. The method further includes applying the composition to one or both of a user's fingers and a swabbing article and contacting the composition to makeup on the skin and rubbing in a circular motion to solvate and/or emulsify the makeup, followed by swiping the contacted skin to remove the makeup, wherein the method does not require cleansing or water rinsing. In some embodiments, the composition is applied with a user's fingers. In some embodiments, the composition is applied with a swabbing article. Some non-limiting examples of swabbing articles include a tissue, a fibrous or fabric pad, such as a tissue or a cotton round, and a sponge.

In some embodiments of the method, the at least one silicone crosspolymer-based emulsifier is present from about 0.1% to about 20%; the at least one polyglyceryl ester with HLB less than 10 is present from about 0.1% to about 20%; the at least one branched or linear liquid alkane with carbon chain length of C11 to C20 is present from about 5% to about 15%; the at least one polar emollient ester with carbon chain length of C12 to C24 is present from about 1% to about 10%; and the water, or water and a water-based hydrating agent or solvent or combination thereof is present from about 65% to about 85%; all amounts by weight, based on the total weight of the composition.

In some embodiments of the method, the composition optionally comprises one or more additives selected from the group consisting of pH adjusters, chelating agents, skin care actives, preservatives, fillers, powders, fragrances, dyes, pigments, and combinations thereof.

In some embodiments of the method, the at least one silicone crosspolymer-based emulsifier of the no-rinse makeup removal composition comprises dimethicone (and) dimethicone/PEG-10/15 crosspolymer present at about 3%; the at least one polyglyceryl ester with HLB less than 10 of the no-rinse makeup removal composition comprises polyglyceryl-6 polyricinoleate present at about 0.2%; the at least one branched or linear liquid alkane with carbon chain length of C11 to C20 of the no-rinse makeup removal composition comprises isohexadecane present at about 7%; the at least one polar emollient ester with carbon chain length of C12 to C24 of the no-rinse makeup removal composition comprises isopropyl palmitate present at about 5%; and the water, or water and a water-based hydrating agent or solvent or combination thereof of the no-rinse makeup removal composition comprises water present from about 65% to about 85% and glycerin present at about 15%.

In some embodiments of the method, the composition further comprises one or more additives selected from the group consisting of sodium chloride, sodium citrate, citric acid, tetrasodium glutamate diacetate, piroctone olamine, hydroxyacetophenone, niacinamide, vitamin C, vitamin E, retinol, resveratrol, derivatives of the foregoing, and combinations thereof.

In some embodiments of the method, the composition is a water-in-oil (silicone) emulsion comprising (a) a water phase that comprises the water, or water and a water-based hydrating agent or solvent or combination thereof, and (b) a silicone oil phase comprising the at least one silicone crosspolymer-based emulsifier, the at least one polyglyceryl ester with HLB less than 10, the at least one branched or linear liquid alkane with carbon chain length of C11 to C20, and the at least one polar emollient ester with carbon chain length of C12 to C24.

In some embodiments the silicone oil phase further comprises one or more oils phase ingredients selected from the group consisting of silicone oils, oil-soluble active ingredients, emollients, and combinations thereof. In some particular examples, the silicone oil phase may further comprise oil soluble actives selected from the group consisting of vitamin E, retinol, resveratrol, derivatives thereof, and combinations thereof. And in some particular examples, the water phase may further comprise water soluble actives selected from the group consisting of vitamin C, niacinamide, derivatives thereof, and combinations thereof.

In some embodiments of the method, the composition has a phase ratio of the total weight of the water phase to the total weight of the silicone oil phase in a range from about 8.0 to about 1.5.

These and other aspects of the invention are set out in the appended claims and described in greater detail in the detailed description of the invention.

This disclosure describes exemplary embodiments in accordance with the general inventive concepts and is not intended to limit the scope of the invention in any way. Indeed, the invention as described in the specification is broader than and unlimited by the exemplary embodiments set forth herein, and the terms used herein have their full ordinary meaning.

It is to be understood that both the foregoing general description and the following detailed description are exemplary and explanatory only and are not restrictive of the disclosure.

DETAILED DESCRIPTION

The inventors provide here a no-rinse makeup removal composition employing a polyglyceryl ester with HLB of less than 10 as a co-emulsifier that is stable and does not cause irritation to the eye during application.

The terms "stable" and "stability" with respect to the emulsion architecture of the inventive composition refers to the composition remaining in a creamy emulsion state and not phase separating as evidenced by the formation of significant fluid droplets. In some embodiments, stable or stability may include the absence of or minimal formation droplets which indicate release of the internal water phase from the emulsion. Stability is evidenced by one or both of visual inspection and by direct measurement of viscosity. In various embodiments, an inventive composition remains stable at temperatures in the range from about 5° C. to about 45° C., over a time period of at least 8 weeks (~two months), and may remain stable for longer, for example for at least three months, or at least four months, or at least six months, and up to about at least 3 years, or any value, range, or sub-range therebetween. The exemplified embodiments of the inventive composition shown in the examples herein demonstrated stability at each of 5° C., 25° C., 37° C., and 45° C. for a period of eight weeks. And such exemplified compositions demonstrated stability for 10 freeze-thaw cycles at −20° C./25° C. As used herein, the term "pass" refers to demonstrated stability at each of 5° C., 25° C., 37° C., and 45° C. for a period of eight weeks, and demonstrated stability for 10 freeze-thaw cycles at −20° C./25° C.

The composition according to the disclosure includes at least one silicone crosspolymer-based emulsifier; at least one polyglyceryl ester with HLB less than about 10; at least one branched or linear liquid alkane with carbon chain length of C11 to C20; at least one polar emollient ester with carbon chain length of C12 to C24; water, or water and a water-based hydrating agent or solvent or combination thereof; and, optionally one or more additives. In some embodiments, the composition has a water phase having a pH that is in a range from about 3-6, and in some embodiments about 5.

The cosmetic composition of the present disclosure includes a water phase and a silicone oil phase formed as a stable water-in-oil (silicone) emulsion that has a phase ratio of the water phase to silicone oil phase of about 8.0 to about 1.5, or alternatively about 7.0 to about 3.5, or alternatively, about 6.0 to about 5.0, or alternatively about 5.5. The phase ratio is calculated by dividing the total weight of the water phase by the total weight of the silicone oil phase.

The inventors developed the inventive composition to address certain deficiencies in the art, in particular consumer need for a makeup removal solution that is minimally dependent on water for cleansing and rinsing, the general desire in the marketplace to provide compositions that are formulated with sustainable, natural and/or green materials, and in particular that lack or minimize use of non-renewable ingredients (e.g., mineral oil and petrol based ingredients) and ingredients that have negative environmental impact (e.g., EDTA that mobilizes heavy metals). Accordingly, the composition is in some embodiments free or essentially free from non-renewable ingredients and ingredients that have negative environmental impact, and in some particular embodiments excludes or is essentially free from ingredients selected from mineral oil, EDTA and combinations thereof. In some embodiments, the composition may include only nominal amounts of petroleum-based ingredients or may be free from petroleum-based ingredients. And in some embodiments, the composition may also be free from ingredients selected from the group consisting of cyclomethicones, phthalates, parabens, sulfates, polyquaternium, microplastics, synthetic dyes, gelling agents, and combinations thereof.

The inventors also sought to address the deficiencies in the art related to the use of co-emulsifiers such as dimethicone and PEG-10 dimethicone, which have been shown by the inventors to provide an emulsion that can breakdown quickly upon application, whereby the internal (water) phase can wick/sip into eyes during application, causing eye irritation to the user, in part due to the relatively low pH of the water phase. The inventors have surprisingly found that the use as a co-emulsifier of polyglyceryl ester having an HLB of about or less than about 10 stabilizes the gel-cream emulsion from breakdown upon application thus essentially eliminating release of water phase and concomitant eye irritation. The inventors have demonstrated that in the absence of the polyglyceryl ester co-emulsifier, the internal (water) phase can wick/sip into eyes during application, causing eye irritation to the user. Further, the inventors have demonstrated that the inventive composition forms a robust emulsion that demonstrates freeze/thaw stability and long term storage stability (at least 8 weeks under accelerated stability study) while retaining the stability upon application. Comparative compositions do not meet both tests of material stability, including freeze/thaw and storage stability, as well as stability on application.

In addition, the inventors have demonstrated through expert evaluations of makeup removal efficacy that exemplified embodiments of the composition according to the disclosure and provide consumer-pleasing, soft and smooth skin feel and demonstrate better performance in removing mascara, in particular, waterproof mascara, as compared with conventional and/or currently marketed makeup removers, and comparative compositions that lack a polyglyceryl co-emulsifier having an HLB of about or less than about 10. And the inventors have demonstrated in bench testing on forearm skin that lipstick and long-wear foundation removal demonstrated at least comparable or better performance as compared with conventional and/or currently marketed makeup removers, and comparative compositions that lack a polyglyceryl co-emulsifier having an HLB of about or less than about 10.

The composition according to the disclosure is a water-in-oil (as exemplified herein, a silicone oil) emulsion that has a cream-gel texture that demonstrates medium to long playtime, providing a pleasant feel when applied and does not immediately absorb into the skin or evaporate. A water-in-oil emulsion is sometimes referred to as a reverse emulsion. The composition is formulated as a "green" or more "sustainable" composition as compared with currently marketed makeup removers, which typically contain mineral oil and/or fossil-derived ingredients and leave behind an unpleasant oily and greasy skin feel after use.

Use of the composition includes applying the composition to one or both of a user's fingers and a swabbing article and contacting the composition to makeup on the skin and rubbing in a circular motion to solvate and/or emulsify the makeup, followed by swiping the contacted skin to remove the makeup, wherein the method does not require cleansing or water rinsing. In some embodiments, the composition is applied with a user's fingers. In some embodiments, the composition is applied with a swabbing article. Some non-limiting examples of swabbing articles include a tissue, a fibrous or fabric pad, such as a cotton makeup pad, and a sponge.

Upon massaging onto the face, the composition demonstrates effective dissolving of eye, face and lip makeup. For example, after application with fingers, the composition may be removed using a tissue or a cotton round which allows the user to gently wipe away the dissolved makeup products. The composition does not require rinsing after application and leaves the skin with a silky and hydrated feel that is not greasy or sticky.

Silicone Crosspolymer-Based Emulsifiers

In accordance with the disclosure, embodiments of the composition include at least one silicone crosspolymer-based emulsifier. In some embodiments, the composition comprises more than one silicone crosspolymer-based emulsifier. In some embodiments, the composition includes two or more silicone crosspolymer-based emulsifiers, wherein the two silicone crosspolymer-based emulsifiers may differ from one another in that one emulsifier has a greater chemical molecular weight than the other emulsifier.

In some embodiments, suitable silicone crosspolymer-based emulsifiers may be chosen from silicone emulsifiers that include functional groups chosen from polyglyceryl, polyethylene glycol, or polypropylene glycol, wherein such silicone crosspolymer-based emulsifiers may be chosen from dimethicone/PEG-10/15 crosspolymer, dimethicone/polyglycerin-3 crosspolymer, polyether-modified cross-linked silicone polymers in dimethicone, including, for example, but not limited to PEG-15/lauryl polydimethylsiloxyethyl dimethicone crosspolymer.

In some embodiments, suitable silicone crosspolymer-based emulsifiers may be chosen from alkyldimethicone copolyol type and dimethicone copolyol type silicone emulsifiers. The at least one silicone crosspolymer-based emulsifier may be chosen from dimethicone/PEG-10/15 crosspolymer, dimethicone/polyglycerin-3 crosspolymer, and combinations thereof.

In some particular embodiments according to the disclosure, the composition comprises a silicone crosspolymer-based emulsifier comprising dimethicone/PEG-10/15 crosspolymer.

In various embodiments, each of the at least one silicone crosspolymer-based emulsifier is present in the composition at a concentration, from about 0.1% to about 20%, and in some embodiments, from about 0.2% to about 15%, and in some embodiments, from about 0.3% to about 10%, and in some embodiments, from about 1% to about 5%, and in some embodiments, from about 2% to about 4%, or any suitable combination, sub-combination, range, or sub-range thereof by weight, based on the weight of the composition. In some embodiments, the composition comprises more than one silicone crosspolymer-based emulsifier, the combination thereof present in the composition at a concentration, from about 0.1% to about 20%, and each of the more than one present in the composition at a concentration from about 0.1% to about 20%, or any suitable combination, sub-combination, range, or sub-range thereof by weight, based on the weight of the composition. One of ordinary skill in the art, however, will appreciate that other ranges are within the scope of the invention.

In some representative examples, a silicone crosspolymer-based emulsifier comprising dimethicone/PEG-10/15 crosspolymer may be present in the composition in a range from about 1% to about 4% or at about 3%.

Thus, in various embodiments, each of the at least one silicone crosspolymer-based emulsifier is present in a composition according to the disclosure from about 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19 to about 20 percent by weight, including increments and ranges there between.

Polyglyceryl Ester Emulsifier

In accordance with the disclosure, embodiments of the composition include a co-emulsifier comprising at least one polyglyceryl ester. In some embodiments, the composition comprises more than one polyglyceryl ester. In some embodiments, the polyglyceryl ester has an HLB less than about 10.

The term "Hydrophilic-Lipophilic Balance" or "HLB," refers to an empirical expression for the relationship of the hydrophilic and hydrophobic groups of an emulsifier. This term is well known to those skilled in the art. See, e.g., "The HLB system. A time-saving guide to Emulsifier Selection" (Pub: ICI Americas Inc., 1984) and US2006/0217283 at [0053].

In some embodiments, the at least one polyglyceryl ester emulsifier has an HLB that is about 10, or less than about 10, and is in some embodiments in a range inclusive of from about 2.5 to about 10, or from about 2.5 to about 9.5, or from about 3 to about 9, and in some examples, the polyglyceryl ester emulsifier has an HLB that is in a range from about 2.5, 2.6, 2.7, 2.8, 2.9, 3, 4, 5, 6, 7, 8, to about 9.9, including increments of about 0.1 therein and therebetween.

In some embodiments, the at least one polyglyceryl ester emulsifier may be selected from the group consisting of polyglyceryl-10 caprate, polyglyceryl-10 caprate, polyglyceryl-10 decastearate, polyglyceryl-10 diisostearate, polyglyceryl-10 dioleate, polyglyceryl-10 distearate, polyglyceryl-10 heptaoleate, polyglyceryl-10 isostearate, polyglyceryl-10 laurate, polyglyceryl-10 myristate, polyglyceryl-10 oleate, polyglyceryl-10 pentaoleate, polyglyceryl-10 pentastearate, polyglyceryl-10 stearate, polyglyceryl-2 caprate, polyglyceryl-2 caprylate, polyglyceryl-2 dipolyhydroxystearate, polyglyceryl-2 laurate, polyglyceryl-2 oleate, polyglyceryl-2 stearate, polyglyceryl-3 caprate, polyglyceryl-3 diisostearate, polyglyceryl-3 methylglucose distearate, polyglyceryl-3 palmitate, polyglyceryl-3 polyricinoleate, polyglyceryl-3 ricinoleate, polyglyceryl-4 caprate, polyglyceryl-4 diisostearate/polyhydroxystearate/sebacate, polyglyceryl-4 isostearate, polyglyceryl-4 laurate, polyglyceryl-5 dioleate, polyglyceryl-5 hexastearate, polyglyceryl-5 laurate, polyglyceryl-5 myristate, polyglyceryl-5 oleate, polyglyceryl-5 stearate, polyglyceryl-5 trimyristate, polyglyceryl-5 trioleate, polyglyceryl-6 caprylate, polyglyceryl-6 polyricinoleate, and combinations thereof.

In some embodiments, a suitable polyglyceryl ester emulsifier having an HLB that is less than about 10 may be selected from the group consisting of polyglyceryl-10 decastearate, polyglyceryl-5 hexastearate, polyglyceryl-10 pentaoleate, polyglyceryl-10 pentastearate, polyglyceryl-10 heptaoleate, polyglyceryl-2 dipolyhydroxystearate, polyglyceryl-4 diisostearate/polyhydroxystearate/sebacate, polyglyceryl-4 isostearate, polyglyceryl-6 polyricinoleate, polyglyceryl-3 diisostearate, polyglyceryl-3 ricinoleate, polyglyceryl-5 trioleate, polyglyceryl-2 oleate, polyglyceryl-5 trimyristate, polyglyceryl-2 caprylate, polyglyceryl-2 laurate, polyglyceryl-3 palmitate, polyglyceryl-3 polyricinoleate, polyglyceryl-2 caprate, polyglyceryl-2 stearate, and combinations thereof.

In some embodiments, a suitable polyglyceryl ester emulsifier having an HLB that is less than about 10 may be selected from the group consisting of polyglyceryl-6 polyricinoleate, polyglyceryl-3 diisostearate, polyglyceryl-2 oleate, polyglyceryl-2 stearate, and combinations thereof.

In some embodiments, a suitable polyglyceryl ester emulsifier having an HLB that is less than about 10 comprises polyglyceryl-6 polyricinoleate.

In some embodiments, the composition excludes emulsifiers with an HLB that is about 10, or greater than about 10, including up to or greater than about 15, wherein the composition is devoid or free from, or essentially free from emulsifiers with an HLB that is about 10 or greater than about 10. In some particular embodiments, the composition excludes polyglyceryl ester emulsifiers with an HLB that is about 10. In some embodiments the composition excludes polyglyceryl ester emulsifiers with an HLB that is greater than 10, or in a range from greater than 10 to about 15, or greater than about 15. In some embodiments polyglyceryl ester emulsifiers with an HLB that is about 10 or greater than about 10 may be selected from the group consisting of polyglyceryl-10 distearate, polyglyceryl-4 laurate, polyglyceryl-10 diisostearate, polyglyceryl-5 dioleate, polyglyceryl-10 dioleate, polyglyceryl-10 isostearate, polyglyceryl-3 methylglucose distearate, polyglyceryl-10 oleate, polyglyceryl-6 caprylate, polyglyceryl-4 caprate, polyglyceryl-10 myristate, polyglyceryl-10 stearate, polyglyceryl-5 oleate, polyglyceryl-10 laurate, polyglyceryl-5 stearate, polyglyceryl-5 myristate, polyglyceryl-5 laurate, polyglyceryl-10 caprate, polyglyceryl-10 caprate, polyglyceryl-3 caprate, and combinations thereof. In some such embodiments, the composition excludes polyglyceryl ester emulsifiers selected from the group consisting of polyglyceryl-10 distearate, polyglyceryl-4 laurate, polyglyceryl-10 diisostearate, polyglyceryl-5 dioleate, polyglyceryl-10 dioleate, polyglyceryl-10 isostearate, polyglyceryl-3 methylglucose distearate, polyglyceryl-10 oleate, polyglyceryl-6 caprylate, polyglyceryl-4 caprate, polyglyceryl-10 myristate, polyglyceryl-10 stearate, polyglyceryl-5 oleate, polyglyceryl-10 laurate, polyglyceryl-5 stearate, polyglyceryl-5 myristate, polyglyceryl-5 laurate, polyglyceryl-10 caprate, polyglyceryl-10 caprate, polyglyceryl-3 caprate, and combinations thereof.

In various embodiments, each of the at least one polyglyceryl ester emulsifier is present in the composition at a concentration, from about 0.1% to about 20%, and in some embodiments from about 0.1% to about 10%, and in some embodiments, from about 0.1% to about 0.5%, or any suitable combination, sub-combination, range, or sub-range thereof by weight, based on the weight of the composition. In some embodiments, the composition comprises more than one polyglyceryl ester, the combination thereof present in the composition at a concentration, from about 0.2% to about 5%, each of the more than one present in the composition at a concentration from about 0.1% to about 4%, or any suitable combination, sub-combination, range, or sub-range thereof by weight, based on the weight of the composition. One of ordinary skill in the art, however, will appreciate that other ranges are within the scope of the invention.

In some representative examples, a polyglyceryl ester co-emulsifier comprising polyglyceryl-6 polyricinoleate may be present in the composition in a range from about 0.1% to about 1% or at about 0.2%.

Thus, in various embodiments, each of the at least one polyglyceryl ester is present in a composition according to the disclosure from about 0.1, 0.2, 0.3, 0.4, 0.5, 0.6, 0.7, 0.8, 0.9, 1, 2, 3, 4, 5, 6, 7, 8, 9, to about 10 percent by weight, including increments and ranges there between.

Branched or Linear Liquid Alkane

In accordance with the disclosure, embodiments of the composition include at least one branched or linear liquid alkane. In some embodiments, the composition comprises more than one branched or linear liquid alkane. In some embodiments, the branched or linear liquid alkane has a carbon chain length of C11 to C20.

In various embodiments, the branched or linear liquid alkane has a carbon chain length of C11 to C20. The branched or linear liquid alkane may be chosen from those with a carbon chain length of from C11 to C20, from C13-C15, from C15 to C19, and C11, C12, C13, C14, C15, C16, C17, C18, C19 and C20. In some particular embodiments, the branched or linear liquid alkane may be chosen from isoparaffins, for instance isododecane (also known as 2,2,4,4,6-pentamethylheptane), isodecane, C15-19 alkane, isohexadecane, undecane, tridecane, and combinations thereof.

In some particular embodiments the at least one branched or linear liquid alkane comprises isohexadecane.

In various embodiments, the at least one branched or linear liquid alkane is present in the composition at a concentration, from about 5% to about 15%, and in some embodiments, from about 5% to about 10%, and in some embodiments, from about 2% to about 5% or any suitable combination, sub-combination, range, or sub-range thereof by weight, based on the weight of the composition. In some embodiments, the composition comprises more than one branched or linear liquid alkane, the combination thereof present in the composition at a concentration, from about 5% to about 15%, and each of the more than one present in the composition at a concentration from about 2% to about 13% or any suitable combination, sub-combination, range, or sub-range thereof by weight, based on the weight of the composition. One of ordinary skill in the art, however, will appreciate that other ranges are within the scope of the invention.

Thus, in various embodiments, each of the at least one branched or linear liquid alkane is present in a composition according to the disclosure from about 2, 3, 4, 5, 6, 7, 8, 9, 10, 11, 12, 13, 14 to about 15 percent, by weight, including increments and ranges therein and there between.

Emollient Ester

In accordance with the disclosure, embodiments of the composition include at least one emollient ester. In some embodiments the at least one emollient ester is a polar emollient ester that has a carbon chain length of C12 to C24. In some embodiments, the composition comprises more than one emollient ester. In some embodiments, the at least one emollient ester is an alkylated alcohol ester.

In some embodiments, the emollient ester is an emollient ester comprising esters of lactic acid and fatty alcohols and comprising 12 or 13 carbon atoms, and combinations thereof.

In some particular embodiments the at least one emollient ester is branched and is an alkylated alcohol ester. In some embodiments the composition comprises two or more branched or linear alkylated alcohol esters. In some such embodiments, the at least one branched or linear alkylated alcohol ester comprises isopropyl myristate and optionally one or more additional branched or linear alkylated alcohol ester.

In some embodiments, suitable emollient esters that may be used according to the disclosure may be chosen from isopropyl myristate, isopropyl palmitate, ethylhexyl palmitate, triethyl citrate, diisopropyl adipate, diisopropyl sebacate, dicaprylyl carbonate, neopentyl glycol diheptanoate, methyl palmitate, 2-ethylhexyl palmitate, hexyl laurate, ethylhexyl laurate, isopropyl laurate, ethylhexyl oleate, ethylhexyl isononanoate, isononyl isononanoate, myristyl myristate, 2-ethylhexyl caprate/caprylate (or octyl caprate/caprylate), isostearyl neopentanoate, cetearyl ethylhexanoate, isopropyl isostearate, diisopropyl sebacate, coco caprylate/caprate, diisopropyl adipate, and combinations thereof.

In some particular embodiments, the at least one emollient ester is selected from the group consisting of isopropyl palmitate, ethylhexyl palmitate, hexyl laurate, triethyl citrate, diisopropyl adipate, diisopropyl sebacate, dicaprylyl carbonate, isopropyl isostearate, isononyl isononanoate, neopentyl glycol diheptanoate, and combinations thereof.

In some particular embodiments, the at least one emollient ester is selected from the group consisting of isopropyl palmitate and ethylhexyl palmitate, and combinations thereof.

In various embodiments, the at least one emollient ester is present from about 1% to about 10% by weight of the composition, and in some embodiments, from about 0.8% to about 8%, and in some embodiments, from about 1% to about 7%, and in some embodiments, from about 2% to about 5%, and in some embodiments, about 5% or about 2%, or any suitable combination, sub-combination, range, or sub-range thereof by weight, based on the weight of the composition. In some embodiments, the composition comprises more than one emollient ester, the combination thereof present in the composition at a concentration, from about 1% to about 20%, and each of the more than one present in the composition at a concentration from about 0.5% to about 10%, or any suitable combination, sub-combination, range, or sub-range thereof by weight, based on the weight of the composition. One of ordinary skill in the art, however, will appreciate that other ranges are within the scope of the invention.

Thus, in various embodiments, each one or a combination of the at least one emollient ester is present in a composition according to the disclosure from about 1, 2, 3, 4, 5, 6, 7, 8, 9, to about 10 percent, by weight, including increments and ranges therein and there between.

Water

In accordance with the various embodiments, water, or water and a water-based hydrating agent or solvent or combination thereof is present in the composition. In some embodiments, water is present in a range from about 65% to about 85%, and in some embodiments, from about 66% to about 85%, and in some embodiments, from about 67% to about 75%, and in some embodiments, from about 68% to about 72%, and in some embodiments, about 68% or any suitable combination, sub-combination, range, or sub-range thereof by weight, based on the weight of the composition. One of ordinary skill in the art, however, will appreciate that other ranges are within the scope of the invention. Thus, water is present, by weight, based on the total weight of the composition, from about 65, 66, 67, 68, 69, 70, 71, 72, 73, 74, 75, 76, 77, 78, 79, 80, 81, 82, 83, 84, to about 85 percent, by weight, including increments and ranges therein and there between. One of ordinary skill in the art, however, will appreciate that other ranges are within the scope of the invention.

The water used may be sterile demineralized water and/or a floral water such as rose water, cornflower water, chamomile water or lime water, and/or a natural thermal or mineral water such as, for example: water from Vittel, water from the Vichy basin, water from Uriage, water from La Roche Posay, water from La Bourboule, water from Enghien-les-Bains, water from Saint Gervais-les-Bains, water from Neris-les-Bains, water from Allevar-les-Bains, water from Digne, water from Maizieres, water from Neyrac-les-Bains, water from Lons-le-Saunier, water from Eaux Bonnes, water from Rochefort, water from Saint Christau, water from Les Fumades, water from Tercis-les-Bains or water from Avene. The water phase may also comprise reconstituted thermal water, that is to say a water comprising trace elements such as zinc, copper, magnesium, etc., reconstituting the characteristics of a thermal water.

The pH of the composition, in particular the water phase of the composition, may be adjusted prior to combining the oil phase with the water phase to avoid the practical difficulty with measuring pH in an internal water phase of the water-in-oil emulsion. Accordingly, the pH of the water phase prior to emulsification can be adjusted with pH adjusters to a pH in a range from about 2 to about 12, and in some embodiments, is from about 3 to about 11, and from about 4 to about 8, and from about 5 to about 6, and in some embodiments about 5. The pH of the water phase can be adjusted by addition of a base (organic or inorganic) to the composition, for example ammonia or a primary, secondary or tertiary (poly)amine, such as monoethanolamine, diethanolamine, triethanolamine, isopropanolamine or 1,3-propanediamine, or alternatively by addition of an inorganic or organic acid, advantageously a carboxylic acid, such as, for example, citric acid.

Hydrating Agents and Solvents

In accordance with the disclosure, embodiments of the composition may include at least one hydrating agent, at least one solvent, or a combination thereof. In some embodiments, the composition comprises more than one hydrating agent, more than one solvent, or a combination thereof. The hydrating agent may be a polyol. In some embodiments, the hydrating agent comprises glycerin.

In some embodiments, suitable hydrating agents that may be used according to the disclosure may be chosen from one or more of polyols, including, for example, glycerin, glycerol, glycols, such as caprylyl glycol, butylene glycol, propylene glycol, isoprene glycol, dipropylene glycol, hexylene glycol and polyethylene glycols, monoethylene glycol, diethylene glycol, diethylene glycol, diethylene glycol, hexylene glycol; glycol ethers such as monopropylene, dipropylene and tripropylene glycol alkyl(C1-C4)ethers; squalane; triacetin; sugars, such as glucose, xylitol, maltitol, sorbitol, sucrose pentaerythritol, inositol; pyrrolidone carboxylic acid (PCA); lactic acid; lithium chloride; acetamide MEA; sodium lactate; urea; dicyanamide; hyaluronic acid; aloe vera; honey; seaweed extract; and combinations thereof.

In some embodiments, suitable solvents that may be used according to the disclosure may be chosen from monoalcohols and polyols, such as ethyl alcohol, isopropyl alcohol, propyl alcohol, benzyl alcohol, and phenylethyl alcohol, or glycols or glycol ethers such as, for example, monomethyl, monoethyl and monobutyl ethers of ethylene glycol, propylene glycol or ethers thereof such as, for example, monomethyl ether of propylene glycol, butylene glycol, hexylene glycol, dipropylene glycol as well as alkyl ethers of diethylene glycol, for example monoethyl ether or monobutyl ether of diethylene glycol. Other suitable examples of organic solvents are ethylene glycol, propylene glycol, butylene glycol, hexylene glycol, propane diol, and glycerin.

In various embodiments, the at least one hydrating agent, solvent or combination thereof, is present from about 5% to about 20% by weight of the composition, and in some embodiments, from about 5% to about 15%, and in some embodiments, from about 10% to about 20%, and in some embodiments, about 15%, or any suitable combination, sub-combination, range, or sub-range thereof by weight, based on the weight of the composition. In some embodiments, the composition comprises more than one hydrating agent, solvent or combination thereof, the combination thereof present in the composition at a concentration, from about 5% to about 20%, and each of the more than one present in the composition at a concentration from about 10% to about 20%, and in some embodiments, about 15% or any suitable combination, sub-combination, range, or sub-range thereof, by weight, based on the weight of the composition. One of ordinary skill in the art, however, will appreciate that other ranges are within the scope of the invention.

Thus, in various embodiments, each of the at least one hydrating agent, solvent or combination thereof is present in a composition according to the disclosure from about 5, 6, 7, 8, 9, 10, 11, 12, 13, 14, 15, 16, 17, 18, 19, to about 20 percent, by weight, including increments and ranges therein and there between.

Optional Additives

The composition may also comprise at least one additive used in the cosmetics field which does not affect the properties of the compositions according to the invention, such as fragrances, preservatives/anti-microbials (for example, potassium sorbate, and caprylyl glycol); actives (for example, hydroxyacetophenone, vitamins, panthenol, tocopherol); oil-soluble active ingredients (for example, tocopherol/vitamin E) and emollients (for example, dimethicone); coloring materials; essential oils; antioxidants; hydroxy acids; citric acid, sodium citrate, sodium chloride; neutralizing, chelating or pH-adjusting agents (for example, triethylamine (TEA), trisodium ethylenediamine disuccinate, and sodium hydroxide), and combinations thereof. In some particular examples, the silicone oil phase may further comprise oil soluble actives selected from the group consisting of vitamin E, retinol, resveratrol, derivatives thereof, and combinations thereof. And in some particular examples, the water phase may further comprise water soluble actives selected from the group consisting of vitamin C, niacinamide, derivatives thereof, and combinations thereof.

In some embodiments the composition may comprise at least one additive selected from the group consisting of pH adjusters, chelating agents, skin care actives, preservatives, fillers, powders, fragrances, dyes, pigments, and combinations thereof. In some particular embodiments the composition may comprise at least one additive selected from the group consisting of sodium chloride, sodium citrate, citric acid, tetrasodium glutamate diacetate, piroctone olamine, hydroxyacetophenone, dimethicone, vitamin E, retinol, resveratrol, vitamin C, niacinamide, derivatives thereof, and combinations thereof.

Although the optional additives are given as examples, it will be appreciated that other optional components compatible with cosmetic applications known in the art may be used that are suitable for a cosmetic composition.

In accordance with the various embodiments, the amount of one or more actives and additives, alone or in combination, when present in the composition according to the disclosure can be present in a range from about 0.0001% to about 20%, and in some embodiments, from about 0.005% to about 0.01%, and in some embodiments, from about 0.01% to about 0.1%, and in some embodiments, from about 0.15% to about 5%, and in some embodiments, from about 0.40% to about 4%, and in some embodiments, from about 0.5% to about 2.5%, and in some embodiments, from about 0.1% to about 0.5% and in some embodiments, from about 1% to about 2%, or any suitable combination, sub-combination, range, or sub-range thereof by weight, based on the total weight of the composition. One of ordinary skill in the art, however, will appreciate that other ranges are within the scope of the invention.

Thus, any one or a combination of actives and additives may be present, each one or the combination present from about 0.0001, 0.0005, 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.10, 0.20, 0.30, 0.40, 0.50, 0.60, 0.70, 0.80, 0.90, 1.0, 2, 3, 4, 5, 6, 7, 8, 9, 10, 11, 12, 13, 14, 15, 16, 17, 18, 19 to about 20 percent, by weight, including increments and ranges therein and there between.

The examples below according to the invention are given by way of illustration and without a limiting nature. The names are the chemical name or the INCI name. The amounts are given therein as % by weight, unless otherwise mentioned.

EXAMPLES

Example 1: Compositions

Various representative embodiments of inventive and comparative compositions are exemplified herein.

TABLE 1

Inventive Compositions 1-4 and Comparative Compositions 1-3

| PH | INCI Name | INV Ex 1 Wt % | INV Ex 2 Wt % | INV Ex 3 Wt % | INV Ex 4 Wt % | COMP Ex 1 Wt % | COMP Ex 2 Wt % | COMP Ex 3 Wt % |
|----|-----------|---------------|---------------|---------------|---------------|----------------|----------------|----------------|
| A | Dimethicone (And) Dimethicone/PEG-10/15 Crosspolymer | 3 | 3 | 3 | 3 | 3 | 3 | 5 |
| A | Polyglyceryl-6 Polyricinoleate | 0.2 | | | | | | |
| A | Polyglyceryl-3 Diisostearate | | 0.2 | | | | | |
| A | Polyglyceryl-2 Oleate | | | 0.2 | | | | |
| A | Polyglyceryl-2 Stearate | | | | 0.2 | | | |
| A | Polyglyceryl-10 Laurate | | | | | | 0.2 | |
| A | Isohexadecane | 7 | 7 | 7 | 7 | 7 | 7 | |
| A | Isopropyl Palmitate | 5 | 5 | 5 | 5 | 5 | 5 | |
| A | Dimethicone | | | | | | | 7 |
| B | Water | 68.39 | 68.39 | 68.39 | 68.39 | 68.59 | 68.39 | 71.92 |
| B | Glycerin | 15 | 15 | 15 | 15 | 15 | 15 | 15 |
| B | Piroctone Olamine | 0.05 | 0.05 | 0.05 | 0.05 | 0.05 | 0.05 | |
| B | Hydroxyacetophenone | 0.5 | 0.5 | 0.5 | 0.5 | 0.5 | 0.5 | |
| B | Sodium Benzoate | | | | | | | 0.2 |
| B | Potassium Sorbate | | | | | | | 0.1 |
| B | Tetrasodium Glutamate Diacetate | 0.1 | 0.1 | 0.1 | 0.1 | 0.1 | 0.1 | |
| B | Sodium Citrate | 0.2 | 0.2 | 0.2 | 0.2 | 0.2 | 0.2 | 0.2 |
| B | Sodium Chloride | 0.5 | 0.5 | 0.5 | 0.5 | 0.5 | 0.5 | 0.5 |
| B | Citric Acid | 0.06 | 0.06 | 0.06 | 0.06 | 0.06 | 0.06 | 0.08 |
| | Total (Wt %): | 100 | 100 | 100 | 100 | 100 | 100 | 100 |
| | Freeze/Thaw Stability (−20° C./25° C., 10 Cycles) | Pass | Pass | Pass | Pass | Border line | Fail | Pass |
| | Stability At 5° C., 25° C., 37° C. & 45° C. (8 Weeks) | Pass | Pass | Pass | Pass | Pass | Fail | Pass |
| | Eye Irritation During Application | No | No | No | No | Yes | Yes | No |
| | Waterproof Mascara Removing Efficacy | Good | Good | Good | Good | Good | N/A | Poor |

Combine oil phase (A) and water phase (B) ingredients in separate beakers and mix well. If needed, apply heat until each phase is homogeneous, and all solids dissolved. Slowly add water phase (B) to oil phase (A) and mix well using an overhead propeller mixer, giving a smooth gel-cream, followed by measurement of viscosity.

In a representative embodiment according to the disclosure the composition comprises dimethicone (and) dimethicone/PEG-10/15 crosspolymer present from about 0.1% to about 10%, and in some embodiments about 3%; one or more of polyglyceryl-6 polyricinoleate, polyglyceryl-3 diisostearate, polyglyceryl-2 oleate, polyglyceryl-2 stearate present from about 0.1% to about 5%, and in some embodiments about 0.2%, isohexadecane present from about 5% to about 15%; and in some embodiments about 7%; isopropyl palmitate present from about 1% to about 10%, and in some embodiments about 5%; glycerin present from about 1% to about 20%, and in some embodiments about 15%; all amounts by weight, based on the total weight of the composition. In some such embodiments, the composition further comprises one or more ingredients selected from the group consisting of sodium chloride, sodium citrate, citric acid, tetrasodium glutamate diacetate, dimethicone, piroctone olamine, hydroxyacetophenone and combinations thereof. According to such embodiments, the composition has a phase ratio of water phase to oil phase in a range from about, and in a specific representative embodiment of about 5.57 (e.g., ~84.8 water phase and ~15.2% oil phase)

Example 2: Expert Evaluation

Demonstration of the effectiveness of inventive compositions vs comparative compositions in stubborn makeup and mascara removal.

A study was conducted to evaluate the effectiveness of the inventive compositions in comparison with comparative compositions, including comparatives having a base formulation that is similar to the inventive compositions except lacking a polyglyceryl ester emulsifier having an HLB less than about 10 or including a polyglyceryl ester emulsifier having an HLB of about 10 or greater than about 10, and comparatives selected from commercially available makeup removers (comparative compositions), having generally similar components. The tested compositions have ingredients as shown in TABLES 1-5.

TABLE 2

Comparative Composition 4-Lancôme Galatéis Douceur (Gentle Cleanser for Face and Eyes), a commercially available emulsion (cream)-based makeup removing product
Ingredients AQUA/WATER
PARAFFINUM LIQUIDUM/MINERAL OIL
ISOPROPYL MYRISTATE
PROPANEDIOL
CARBOMER
PEG-32
PEG-60 HYDROGENATED CASTOR OIL

TABLE 2-continued

Comparative Composition 4-Lancôme Galatéis Douceur
(Gentle Cleanser for Face and Eyes), a commercially available
emulsion (cream)-based makeup removing product
Ingredients SALICYLIC ACID
DISODIUM EDTA
PARFUM/FRAGRANCE
SODIUM HYDROXIDE
DISODIUM COCOAMPHODIACETATE
LINALOOL
HYDROXYCITRONELLAL
BENZYL ALCOHOL
CINNAMYL ALCOHOL
GERANIOL
ANANAS SATIVUS FRUIT EXTRACT/PINEAPPLE FRUIT EXTRACT
HEXYL CINNAMAL
EUGENOL
PAPAIN
CITRONELLOL
CI 77007/ULTRAMARINES
SILICA

TABLE 3

Comparative Composition 5-NEUTROGENA
Makeup Remover Cleansing Towelettes
Ingredients Water
Isononyl Isononanoate
Isostearyl Palmitate
Cetyl Ethylhexanoate
Cyclopentasiloxane
Pentaerythrityl Tetraethylhexanoate
Hexylene Glycol
PEG-6 Caprylic/Capric Glycerides
Phenoxyethanol
Sucrose Cocoate
Carbomer
PEG-4 Laurate
Fragrance
Sodium Hydroxide
Benzoic Acid
Dehydroacetic Acid
Iodopropynyl Butylcarbamate
Ethylhexylglycerin

TABLE 4

Comparative Composition 6-GARNIER SkinActive
Micellar Cleansing Water All-in-1
Cleanser & Makeup Remover (Mono-phase)
Ingredients AQUA/WATER
HEXYLENE GLYCOL
GLYCERIN
POLOXAMER 184
DISODIUM COCOAMPHODIACETATE
DISODIUM EDTA
POLYAMINOPROPYL BIGUANIDE

TABLE 5

Comparative Composition 7-GARNIER SkinActive
Micellar Cleansing Water All-in-1
Cleanser & Waterproof Makeup Remover (Bi-Phase)
Ingredients

WATER/AQUA
CYCLOPENTASILOXANE
ISOHEXADECANE

TABLE 5-continued

Comparative Composition 7-GARNIER SkinActive
Micellar Cleansing Water All-in-1
Cleanser & Waterproof Makeup Remover (Bi-Phase)
Ingredients POTASSIUM PHOSPHATE
HEXYLENE GLYCOL
POLYAMINOPROPYL BIGUANIDE
SODIUM CHLORIDE
DIPOTASSIUM PHOSPHATE
DECYL GLUCOSIDE
DISODIUM EDTA In the study, the tested compositions were used by a trained/expert aesthetician to remove mascara (Maybelline™ Colossal Big Shot Waterproof Mascara).

The makeup removal efficacy was determined by following a protocol under which the aesthetician applied the stubborn makeup products on six (6) Caucasian women. After 30 min, the aesthetician removed the makeup with test products (inventive and comparative), using 3 cotton rounds each soaked with 2 ml of the test composition for mascara removal. The degree of removal was assessed by the amount of residual makeup that was removed by using Lancôme™ Bi-Facil™ Makeup Remover (a two-phase makeup removal product), 2 mL on a cotton pad for up to 6 cotton pads. The higher the makeup removal efficacy of the test formula would require fewer cotton pads with Bi-Facil™, as there would be less residual makeup. The makeup removal efficacy data are represented in Table 6.

TABLE 6

Waterproof Mascara Removal Efficacy (scale of 0 to 6:
6 being complete removal, and 0 being no removal)

| Test Composition | Waterproof Mascara |
| --- | --- |
| Inventive Ex. 1 | 3.1 |
| Comparative Ex. 3 | 0.5 |
| Lancôme Galatéis Douceur (Comparative Ex. 4) | 0.7 |
| Neutrogena Cleansing Wipes (Comparative Ex. 5) | 0.2 |
| Garnier Micellar Water, Mono-phase (Comparative Ex. 6) | 0.5 |
| Garnier Micellar Water, Bi-phase (Comparative Ex. 7) | 2.3 |

As shown, the inventive composition outperformed all of the tested comparative compositions. Comparative Example 1, which has essentially the same base composition as Inventive composition 1 but lacks a co-emulsifier, passes longer term stability test in multiple temperature chambers for 8 weeks, however, it exhibits borderline freeze/thaw cycle stability and showed water droplets on the surface of the formulation bulk. As such, and as revealed in the study, when applying Comparative Example 1 in removing mascara, the user experiences stinging sensation in the eyes due to the leakage of water phase. Comparative Example 2, which has essentially the same base composition as Inventive composition but utilizes a polyglyceryl ester emulsifier of HLB value of 15 as the co-emulsifier. While the emulsion can form initially, the formula separated during freeze/thaw cycles and its viscosity drops over time. Applying Comparative Example 2 also causes irritation in the eye area; thus it is difficult to assess its makeup removing efficacy. Comparative Example 3 uses dimethicone as the emollient. While the formula is stable and provides good skin feel and no irritation to the eyes, it does not provide efficacy in removing eye makeup.

While the disclosure has been described with reference to described embodiments, it will be understood by those skilled in the art that various changes may be made and equivalents may be substituted for elements thereof without departing from the scope of the disclosure. In addition, many modifications may be made to adapt a particular situation or material to the teachings of the disclosure without departing from the essential scope thereof. Therefore, it is intended that the disclosure is not limited to the particular embodiment disclosed as the best mode contemplated for carrying out this disclosure, but that the disclosure will include all embodiments falling within the scope of the appended claims.

The articles "a" and "an," as used herein, mean one or more when applied to any feature in embodiments of the present disclosure described in the specification and claims. The use of "a" and "an" does not limit the meaning to a single feature unless such a limit is specifically stated. The article "the" preceding singular or plural nouns or noun phrases denotes a particular specified feature or particular specified features and may have a singular or plural connotation depending upon the context in which it is used. The adjective "any" means one, some, or all indiscriminately of whatever quantity.

"At least one," as used herein, means one or more than one, including two or more than two, and thus includes individual components as well as mixtures/combinations.

The transitional terms "comprising", "consisting essentially of" and "consisting of", when used in the appended claims, in original and amended form, define the claim scope with respect to what unrecited additional claim elements or steps, if any, are excluded from the scope of the claim(s). The term "comprising" is intended to be inclusive or open-ended and does not exclude any additional, unrecited element, method, step or material. The term "consisting of" excludes any element, step or material other than those specified in the claim and, in the latter instance, impurities ordinarily associated with the specified material(s). The term "consisting essentially of" limits the scope of a claim to the specified elements, steps or material(s) and those that do not materially affect the basic and novel characteristic(s) of the claimed disclosure. All materials and methods described herein that embody the present disclosure can, in alternate embodiments, be more specifically defined by any of the transitional terms "comprising," "consisting essentially of," and "consisting of."

The terms "free" and "devoid" indicates that no reliably measurable excluded material is present in the composition, typically 0% by weight, based on the total weight of the composition. The term "essentially free" means that, while it prefers that no excluded material is present in the composition, it is possible to have very small amounts of the excluded material in the composition of the invention, provided that these amounts do not materially affect the advantageous properties of the composition. In particular, "essentially free" means that excluded material can be present in the composition at an amount of less than about 0.1% by weight, based on the total weight of the composition.

The term "about," means within 10% of the indicated number (e.g., "about 10%" means 9%-11% and "about 2%" means 1.8%-2.2%).

All percentages and ratios are calculated by weight unless otherwise indicated. All percentages are calculated based on the total composition unless otherwise indicated. Generally, unless otherwise expressly stated herein, "weight" or "amount" as used herein with respect to the percent amount of an ingredient refers to the amount of the raw material comprising the ingredient, wherein the raw material may be described herein to comprise less than and up to 100% activity of the ingredient. Therefore, weight percent of an active in a composition is represented as the amount of raw material containing the active that is used and may or may not reflect the final percentage of the active, wherein the final percentage of the active is dependent on the weight percent of active in the raw material.

The terms "weight percent" and "wt %" may be used interchangeably and mean percent by weight, based on the total weight of a composition, article or material, except as may be specified with respect to, for example, a phase, or a system that is a component of a composition, article or material. All ranges and amounts given herein are intended to include subranges and amounts using any disclosed point as an end point. Thus, a range of "1% to 10%, such as 2% to 8%, such as 3% to 5%," is intended to encompass ranges of "1% to 8%," "1% to 5%," "2% to 10%," and so on. A range given of "about 1% to 10%" is intended to have the term "about" modifying both the 1% and the 10% endpoints. Further, a range is intended to be inclusive of the endpoints of and all numbers in the range except as expressly stated otherwise. Further still, it is understood that when an amount of a component is given, it is intended to signify the amount of the active material unless otherwise specifically stated.

Notwithstanding that the numerical ranges and parameters setting forth the broad scope of the disclosure are approximations, unless otherwise indicated the numerical values set forth in the specific examples are reported as precisely as possible. Any numerical value, however, inherently contains certain errors necessarily resulting from the standard deviation found in their respective testing measurements. The example that follows serves to illustrate embodiments of the present disclosure without, however, being limiting in nature.

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls.

What is claimed is:

1. A no-rinse makeup removal composition, comprising:
   i. at least one silicone crosspolymer-based emulsifier that comprises dimethicone/PEG-10/15 crosspolymer;
   ii. at least one polyglyceryl ester with HLB less than 10 that comprises polyglyceryl-6 polyricinoleate;
   iii. at least one branched or linear, liquid alkane with carbon chain length of C11 to C20 that comprises isohexadecane;
   iv. at least one polar emollient ester with carbon chain length of C12 to C24 that comprises ethylhexyl palmitate or isopropyl palmitate or a combination thereof;
   v. water, or a combination of water and a water-based hydrating agent or solvent; and,
   vi. optionally one or more additives
      wherein the composition is a water-in-oil (silicone) emulsion comprising (a) a water phase that comprises the water, or the combination of water and a water-based hydrating agent or solvent, and (b) a silicone oil phase comprising the at least one silicone crosspolymer-based emulsifier, the at least one polyglyceryl ester with HLB less than 10, the at least one branched or linear, liquid alkane with carbon chain length of C11 to C20, and the at least one polar emollient ester with carbon chain length of C12 to C24, the composition excluding cyclomethicones, and wherein the composition has a phase ratio of the total weight of the water phase to the total weight of the silicone oil phase in a range from about 8.0 to about 1.5.

2. The no-rinse makeup removal composition according to claim 1, wherein the at least one silicone crosspolymer-based emulsifier additionally includes dimethicone/polyglycerin-3 crosspolymer, and wherein the at least one polyglyceryl ester with HLB less than 10 includes at least one additional polyglyceryl ester with HLB less than 10 that is selected from the group consisting of polyglyceryl-3 diisostearate, polyglyceryl-2 oleate, polyglyceryl-2 stearate and combinations thereof.

3. The no-rinse makeup removal composition according to claim 1, wherein the at least one branched or linear, liquid alkane with carbon chain length of C11 to C20 includes at least one additional branched or linear, liquid alkane with carbon chain length of C11 to C20 that is selected from the group consisting of isododecane, undecane, tridecane, C15-19 alkane, and combinations thereof, and wherein the at least one polar emollient ester with carbon chain length of C12 to C24 includes at least one additional polar emollient ester with carbon chain length of C12 to C24 that is selected from the group consisting of isopropyl myristate, hexyl laurate, triethyl citrate, diisopropyl adipate, diisopropyl sebacate, dicaprylyl carbonate, isopropyl isostearate, isononyl isononanoate, neopentyl glycol diheptanoate and combinations thereof.

4. The no-rinse makeup removal composition according to claim 1, wherein the at least one silicone crosspolymer-based emulsifier is present from about 0.1% to about 10%, by weight of the composition.

5. The no-rinse makeup removal composition according to claim 1, wherein the at least one polyglyceryl ester with HLB less than 10 is present from about 0.1% to about 5%, by weight of the composition.

6. The no-rinse makeup removal composition according to claim 1, wherein the at least one branched or linear, liquid alkane with carbon chain length of C11 to C20 is present from about 5% to about 15% by weight of the composition.

7. The no-rinse makeup removal composition according to claim 1, wherein the at least one polar emollient ester with carbon chain length of C12 to C24 is present from about 1% to about 10% by weight of the composition.

8. The no-rinse makeup removal composition according to claim 1, wherein the water, or the combination of water and a water-based hydrating agent or solvent is present from about 65% to about 85% by weight of the composition.

9. The no-rinse makeup removal composition according to claim 1, wherein the water, or the combination of water and a water-based hydrating agent or solvent comprises water and at least one water-based hydrating agent, the at least one water-based hydrating agent present from about 5% to about 20% by weight of the composition.

10. The no-rinse makeup removal composition according to claim 1, wherein the composition has a phase ratio of the total weight of the water phase to the total weight of the silicone oil phase in a range from about 7.0 to about 3.5.

11. The no-rinse makeup removal composition according to claim 10, wherein the silicone oil phase further comprises one or more oil phase ingredients selected from the group consisting of silicone oils, oil-soluble active ingredients, emollients, and combinations thereof, and one or both of the water and silicone oil phases optionally includes the one or more additives, the one ore more additives selected from the group consisting of pH adjusters, chelating agents, skin care actives, preservatives, fillers, powders, fragrances, dyes, pigments, and combinations thereof.

12. The no-rinse makeup removal composition according to claim 1, wherein the at least one silicone crosspolymer-based emulsifier comprises dimethicone (and) dimethicone/PEG-10/15 crosspolymer present from about 0.1% to about 10%; the at least one polyglyceryl ester with HLB less than 10 comprises polyglyceryl-6 polyricinoleate present from about 0.1% to about 5%; the at least one branched or linear, liquid alkane with carbon chain length of C11 to C20 comprises isohexadecane present from about 5% to about 15%; the at least one polar emollient ester with carbon chain length of C12 to C24 comprises isopropyl palmitate present from about 1% to about 10%; and the water, or the combination of water and a water-based hydrating agent or solvent comprises water and at least one water-based hydrating agent, the at least one water-based hydrating agent present from about 5% to about 20% by weight of the composition; all amounts by weight, based on the total weight of the composition.

13. The no-rinse makeup removal composition according to claim 1, wherein the silicone oil phase further comprises one or more oil phase ingredients selected from the group consisting of oil-soluble active ingredients, emollients, and combinations thereof.

14. A method for removing makeup, comprising:
   a. selecting a no-rinse makeup removal composition according to claim 1,
   b. applying the composition to a swabbing article and contacting the composition to makeup on the skin in a circular motion to solvate and emulsify the makeup; and
   c. swiping the contacted skin to remove the makeup, wherein the method does not require a secondary cleansing or water rinsing.

15. The method according to claim 14, wherein the at least one silicone crosspolymer-based emulsifier is present from about 0.1% to about 10%; the at least one polyglyceryl ester with HLB less than 10 is present from about 0.1% to about 5%; the at least one branched or linear, liquid alkane with carbon chain length of C11 to C20 is present from about 5% to about 15%; the at least one polar emollient ester with carbon chain length of C12 to C24 is present from about 1% to about 10%; and the water, or the combination of water and a water-based hydrating agent or solvent is present from about 65% to about 85%; all amounts by weight, based on the total weight of the composition, and wherein the composition optionally comprises one or more additives selected from the group consisting of pH adjusters, chelating agents, skin care actives, preservatives, fillers, powders, fragrances, dyes, pigments, and combinations thereof.

16. The method according to claim 15, wherein in the no-rinse makeup removal composition, the at least one silicone crosspolymer-based emulsifier comprises dimethicone (and) dimethicone/PEG-10/15 crosspolymer present at about 3%; the at least one polyglyceryl ester with HLB less than 10 comprises polyglyceryl-6 polyricinoleate present at about 0.2%; the at least one branched or linear, liquid alkane with carbon chain length of C11 to C20 comprises isohexadecane present at about 7%; the at least one polar emollient ester with carbon chain length of C12 to C24 comprises isopropyl palmitate present at about 5%; and the water, or the combination of water and a water-based hydrating agent or solvent comprises water present from about 65% to about 85% and glycerin present at about 15%, and wherein the composition further comprises one or more additives selected from the group consisting of sodium chloride, sodium citrate, citric acid, tetrasodium glutamate diacetate, piroctone olamine, hydroxyacetophenone, and combinations thereof, by weight of the composition wherein the composition has a phase ratio of the total weight of the water phase to the total weight of the silicone oil phase in a range from about 7.0 to about 3.5, and wherein the silicone oil phase further comprises one or more oils phase ingredients selected from the group consisting of silicone oils, oil-soluble active ingredients, emollients, and combinations thereof.

17. The no-rinse makeup removal composition according to claim 1, wherein
    i. the at least one silicone crosspolymer-based emulsifier is present from about 0.3% to about 10% by weight of the composition;
    ii. the at least one polyglyceryl ester with HLB less than 10 is present from about 0.1% to about 0.5% by weight of the composition;
    iii. the at least one branched or linear, liquid alkane with carbon chain length of C11 to C20 is present from about 5% to about 10% by weight of the composition; and
    iv. the at least one polar emollient ester with carbon chain length of C12 to C24 is present from about 2% to about 7% by weight of the composition.

18. The no-rinse makeup removal composition according to claim 1, wherein the composition is essentially free of EDTA.

19. A no-rinse makeup removal composition comprising: at least one silicone crosspolymer-based emulsifier that comprises dimethicone (and) dimethicone/PEG-10/15 crosspolymer present at about 3%; at least one polyglyceryl ester with HLB less than 10 that comprises polyglyceryl-6 polyricinoleate present at about 0.2%; at least one branched or linear, liquid alkane with carbon chain length of C11 to C20 that comprises isohexadecane present at about 7%; at least one polar emollient ester with carbon chain length of C12 to C24 that comprises isopropyl palmitate present at about 5%; and water, or a combination of water and a water-based hydrating agent or solvent that comprises water and at least one water-based hydrating agent that comprises glycerin present at about 15%, wherein the composition further comprises one or more additives selected from the group consisting of sodium chloride, sodium citrate, citric acid, tetrasodium glutamate diacetate, piroctone olamine, hydroxyacetophenone, and combinations thereof.

* * * * *